United States Patent [19]

Gottlieb

[11] Patent Number: 4,774,176

[45] Date of Patent: Sep. 27, 1988

[54] SENSITIVE TESTS FOR MALIGNANCIES BASED ON DNA DETECTION

[76] Inventor: A. Arthur Gottlieb, 5915 Pitt St., New Orleans, La. 70115

[21] Appl. No.: 650,218

[22] Filed: Sep. 13, 1984

Related U.S. Application Data

[63] Continuation of Ser. No. 389,381, Jun. 17, 1982, Pat. No. 4,490,472.

[51] Int. Cl.$^4$ .................... C12Q 1/68; G01N 33/566; G01N 33/543
[52] U.S. Cl. .......................................... 435/6; 436/518; 436/813; 436/808; 436/501; 435/803; 435/810
[58] Field of Search .................. 536/27; 435/4, 6, 91, 435/176, 179, 188, 803, 810; 436/63, 64, 501, 94, 177, 178, 264, 529, 800, 804, 805, 808, 813, 824, 825; 935/6, 77; 427/2

[56] References Cited

U.S. PATENT DOCUMENTS

| | | | |
|---|---|---|---|
| 4,270,924 | 6/1981 | Crooke et al. | 436/64 |
| 4,286,964 | 9/1981 | Seed | 935/78 X |
| 4,358,535 | 11/1982 | Falkow et al. | 436/504 X |
| 4,395,486 | 7/1983 | Wilson et al. | 935/78 X |
| 4,455,380 | 6/1984 | Adachi | 436/501 X |
| 4,490,472 | 12/1984 | Gottlieb | 436/504 |
| 4,493,899 | 1/1985 | Smith et al. | 436/508 |

OTHER PUBLICATIONS

Gottlieb, A. A. et al, *Cancer Research*, vol. 40, 1980, pp. 758–770.

*Primary Examiner*—Charles F. Warren
*Assistant Examiner*—Jeremy M. Jay

[57] ABSTRACT

A more convenient, more sensitive test for detection of certain malignancies in human and animal subjects is disclosed. Sera from test subjects is mixed with labeled DNA in the presence of an enzyme-conjugated matrix. Sera from normal and cancerous subjects react differently with the matrix, permitting a diagnosis of the subject.

13 Claims, 1 Drawing Sheet

SENSITIVE TESTS FOR MALIGNANCIES BASED ON DNA DETECTION

This is a continuation of a Ser. No. 389,381, June 17, 1982, U.S. Pat. No. 4,490,472.

BACKGROUND OF THE INVENTION

1. Field of the Invention

The present invention relates to improved means of testing human and animal subjects for the presence of certain malignancies. More specifically, an embodiment is disclosed that permits the diagnosis of several types of lymphoid malignancies (leukemias).

2. Detailed Discussion of Background and Prior Art

The inventor has discovered that blood sera and other body fluids collected from mice or human subjects with certain malignancies contain certain unique double-stranded DNA molecules, which have the ability to selectively inhibit certain members of the group of enzymes known as DNA polymerases. These DNA molecules are absent from sera obtained from mice or human subjects who do not have these malignancies. The inventor has, with others, described this discovery and these DNAs, with related information, in a series of papers. See: Perisco and Gottlieb, *DNA Polymerases of Myeloma*, Nature New Biology 239: 173–76 (1972); Gottlieb, Smith, Plescia, Perisco, and Nicholson, *Inhibitor of DNA Polymerase*, Nature 246: 480–82 (1973); Gottlieb, Smith, Plescia, Nicholson, Bowers, Pankuch, and Berkoben, *An Inhibitor of DNA Polymerase*, in Fundamental Aspects of Neoplasia, ch. 20, pp. 269–77 (1975); Gottlieb, Gottlieb, and Nicholson, *Inhibition of DNA Polymerase by Sera*, in Bibliotheca Haematologica, No. 43 (Basel 1976); Brennessel, Buhrer, and Gottlieb, *Use of Insoluble Heparin for Isolation of DNA Polymerase*, Analytical Biochemistry 87: 411–17 (1978); Gottlieb, Chang, Buhrer, and Brennessel, *Isolation from Murine Myeloma and Leukemia Cells of a Selective Inhibitor of DNA Polymerase*, Cancer Research 40: 758–70 (1980). These DNAs are referred to herein collectively as "DNA-L".

DNA-L is a mixture of DNA molecules in the 150 to 300 base pair range. Any of these DNA molecules can selectively inhibit R-1 DNA polymerase. The inventor has separated these DNA molecules into two groups, DNA-1 and DNA-2, which can be separated by chromatography. Similar DNA molecules can be extracted from normal liver, but not from normal blood sera. Normal blood sera lack these DNAs, and sera of patients with leukemia have the DNAs. All of the foregoing DNA-L molecules can be cloned and used in the test procedures described herein.

There are two groups of DNA-L molecules of principal interest herein, each of which contains a limited but undetermined number of different molecules. The DNAs of principal interest herein may be termed "DNA-1" and "DNA-2." It is believed that these DNAs may play an important role in the replication of leukemic cells. DNA-1 and DNA-2 have important common properties.

Both DNA-1 and DNA-2 have been demonstrated to exert selective inhibition for R-1 DNA polymerase enzyme, which is found in murine myeloma and may exist in other tumors and normal tissues. (The inhibition is "selective," in that other DNAs may well exist that will indiscriminately inhibit this and other polymerase enzymes. The DNAs of interest inhibit the R-1 DNA polymerase and do not inhibit other known polymerase enzymes.) The R-1 DNA polymerase enzyme may be recovered from murine MOPC-21 myeloma tumor by procedures described in Analytic Biochemistry 87: 411–17 (1978), supra. The fact that the enzyme is of murine origin is immaterial, because it reacts with DNAs of interest from both human and murine sources.

Present tests for leukemia, such as bone marrow tests, may be inconvenient and traumatic for the patient. Also, their sensitivity is limited to detecting the presence of substantial numbers of cancer cells, so that early cases of leukemia may escape detection. The procedures of this invention do not involve production of antibodies, as in the work of Bogoch, Detection of Malignant Tumor Cells, U.S. Pat. No. 4,298,590 (Nov. 3, 1981). Such laborious and indirect methods of measurement are not used herein.

SUMMARY OF THE PRESENT INVENTION

The test procedure of this invention determines the presence of DNAs (hereafter "cancer DNAs") whose presence in body fluids in appreciable quantities is associated with the growth of malignant cells and whose presence thus indicates the presence in the body of malignant cells. The test procedure does so by subjecting a medium that possibly contains cancer DNAs to potential "competitive binding," the competitor (sometimes termed the "DNA probe") being a known quantity of such a cancer DNA. The medium described below is blood serum, which the inventor prefers to use because of its convenience and accessibility, but other media, such as ascites fluid and lymph, also contain the cancer DNAs discussed herein and may contain other cancer DNAs of similar interest. Cerebrospinal fluid, duodenal fluid, gastric fluid, pleural fluid, urine, saliva, other mucous secretions, and other body fluids may also contain similar DNAs.

In the test described herein, the serum to be tested for a cancer DNA is mixed with a known quantity of "labeled" cancer DNA (DNA probe). The mixture is "introduced" to what is described below as an "Enzyme-Conjugated Matrix," which will bind with the cancer DNA but not with other kinds of DNA that may be present, or with other substances present. Then a test procedure is used to determine how much labeled DNA (DNA probe) was taken up and bound to the Enzyme-Conjugated Matrix or left behind in the residue of the test mixture.

When relatively less labeled DNA is taken up by the Enzyme-Conjugated Matrix, the reason is that unlabeled similar DNA from the test serum competed for, and excluded the labeled DNA from, the enzyme sites on the Enzyme-Conjugated Matrix. When relatively more labeled DNA is taken up by the Enzyme-Conjugated Matrix, the reason is that unlabeled DNA similar to the labeled DNA was not present in the test serum to compete for, and thus exclude the labeled DNA from, the sites on the Enzyme-Conjugated Matrix.

A principal contribution of the present invention lies in the discovery of sensitive test procedures that permit early detection of leukemia or relapses, and that permit determination of whether a remission is in effect. These techniques, it is believed, are so sensitive as to detect the presence of as few as 250 malignant cells in a mouse or, by extrapolation on a blood and body weight basis, approximately 750,000 malignant cells in a human being. The latter figure may be contrasted with the approximately $4.5 \times 10^{10}$ cells present in the typical human blood stream, so that the test detects approximately 15 parts per million. Present leukemia tests, in contrast, are believed capable of detecting leukemia only when as many as approximately 10,000,000 malignant cells, or approximately 220 parts per million, are already established in the body.

There are several reasons why a more sensitive test is desired, that will permit earlier detection of malignancies such as leukemia. First, it is believed that earlier use of treatment will cause less harm to be done to the patient's body and possibly increase patient survival rates. But an early diagnosis is necessary before such therapy, which may be debilitating, is indicated. Second, leukemias are very alarming diseases. Mononucleosis is often confused with leukemia, because of similarity in symptoms. It is important to obtain a negative diagnosis of leukemia promptly in cases of mononucleosis, because of the severe adverse psychological effects on young patients and their parents of a diagnosis of possible leukemia.

The method of the invention is also cheaper, more convenient, less traumatic to the patient, more readily adaptable to large-scale screening, and more practical to use in frequent testing of the same patient—relative to existing procedures.

In the inventor's preferred usage, in this context, the term "leukemia" includes not only such murine leukemias as MCDV 12 and L 1211, but also multiple myeloma and other malignancies of the human or animal lymphoid system. Accordingly, the following discussion and claims should be read in the light of such usage of the term "leukemia."

DETAILED DESCRIPTION OF PREFERRED EMBODIMENT

Figure 1:
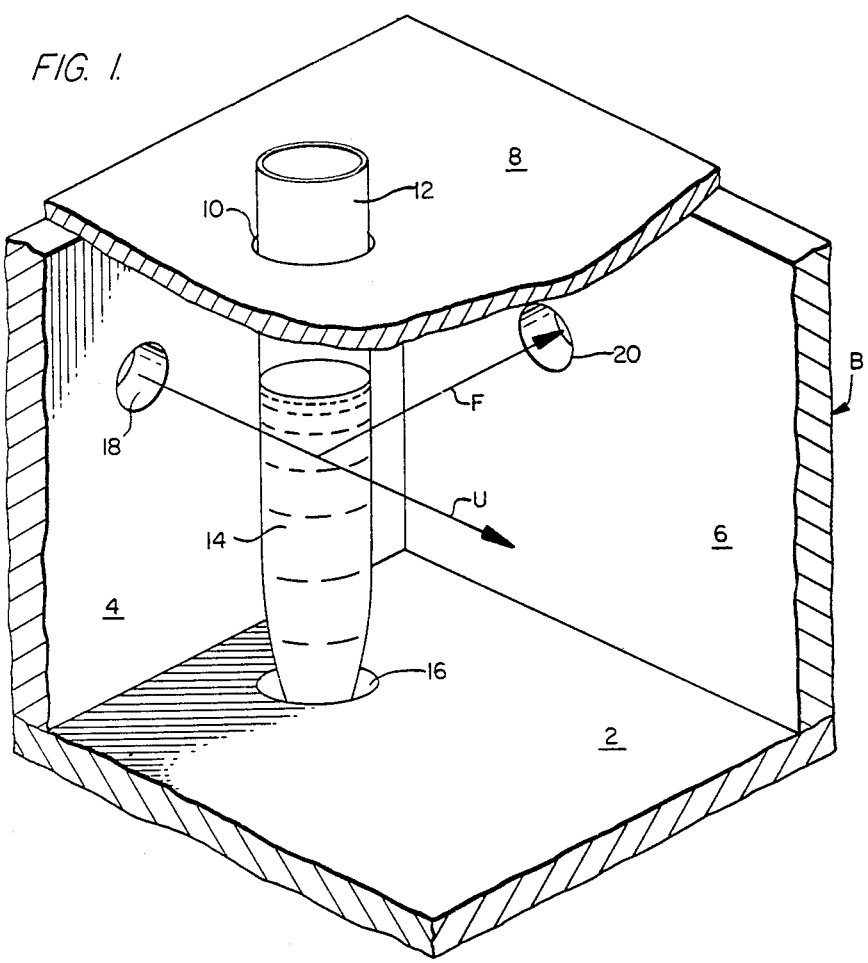
Figure 2:
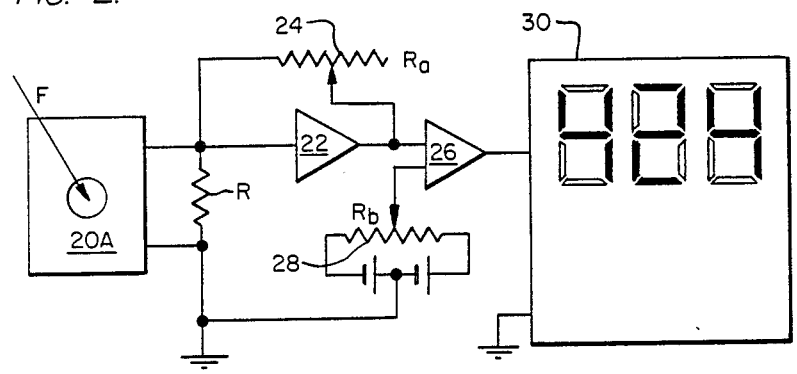

The test procedure of this invention is a new and improved means of testing for the presence of malignancies, such as leukemia, associated with particular DNAs. In the case of leukemia, the DNA is DNA-L. The inventor believes that other DNAs may exist, similarly related to other malignancies, and lending themselves to similar test procedures.

I. Preparation of Test Sample

The initial step in the inventor's leukemia test is to extract a quantity of blood (or other body fluid) from the test subject, remove cells by centrifugation to prepare serum (in the case of blood), and prepare a test sample from it. To do so, the body fluid sample is treated with 70% ammonium sulfate to precipitate all protein in the sample. The precipitate is discarded and the supernatant fluid is retained. The latter is substantially purified by centrifugation and dialysis. The resulting clear liquid is the "test sample."

EXAMPLE

Test Sample 0.5 ml blood serum is obtained from a laboratory mouse. A saturated aqueous solution of ACS Reagent Grade $(NH_4)_2SO_4$ is added dropwise to the sample until a final concentration of 70% $(NH_4)_2SO_4$ is achieved. The resultant protein precipitate is removed by centrifugation at 1,700 g for 10 minutes, and is discarded. Approximately 1 ml of clear supernatant fluid is thus produced. It is dialyzed in a 12,000 M.W. dialysis sac against 0.01M Tris.HCL buffer (pH 7.8) overnight at 4°

C. The material remaining in the dialysis sac (approximately 1 ml) is the test sample.

Tests may be performed directly on the test sample of Example 1, but the inventor considers it preferable first to purify it further with a "purification matrix," as described below in Example 8B.

II. Preparation of DNA-L

The inventor has described generally the extraction of DNA-L in Cancer Research 40: 758 (1980), supra. DNA-L is a mixture of DNAs. It is possible to use a DNA-L mixture of DNA-1 and DNA-2 to perform the tests described here. That procedure requires use of a product made up of DNA-1 and DNA-2 in unknown and variable proportions. The inventor has therefore developed an optional procedure for separating DNA-1 and DNA-2 from one another. The inventor has also developed a procedure for obtaining clones of individual DNAs within the DNA-L group.

The procedure for separation of DNA-1 and DNA-2 involves subjecting a human or murine test sample, prepared as previously described in Example 1 and taken from a subject known to have leukemia or myeloma, to sequential chromatography. The chromatography is performed on an Enzyme-Conjugated Matrix. This is a matrix to which an enzyme can be bound. One example is an agarose-based, gel-like substance to which an enzyme can be covalently bound in a stable fashion, so that it is available for further use. Another example is microspheres. Both examples are described below.

A general procedure is suggested for preparation of Enzyme-Conjugated Matrices in *Affinity Chromatography, Principles and Methods* (Pharmacia). The resin selected must be one to which the enzyme of interest will bind. The Pharmacia product, CNBr-Sepharose, has been found suitable for R-1 DNA polymerase, and the inventor has developed a procedure for preparing such a matrix. The inventor is aware of no published or otherwise previously known procedure for preparing an Enzyme-Conjugated Matrix in which R-1 DNA polymerase is bound to the matrix.

The following procedure differs from the general procedure cited above, in several important respects. The inventor has discovered that, to prepare a Sepharose gel Enzyme-Conjugated Matrix effective for use in the procedures and tests described below, i.e., to get repeatable and consistent results, it is important or perhaps even necessary to pretreat the Enzyme-Conjugated Matrix with buffer solution containing DNA, such as alkali-denatured salmon sperm DNA (Millipore Corp.). The matrix treated in this way is washed with buffer solution. If this pretreatment process with DNA is not carried out, the Sepharose gel Enzyme-Conjugated Matrix apparently will not react specifically with DNA-L, so that inconsistent test results are obtained. It is believed that the DNA pretreatment ties up and thus eliminates from the procedure that follows those binding sites on the Enzyme-Conjugated Matrix that have a general or nonselective affinity for DNA, as contrasted with the sites that have a selective affinity for DNA-L. It is believed that use of such pretreatment procedure in connection with such matrices is unknown in the prior art. Although the necessity of this step has been shown only for the enzyme conjugated to Sepharose, it is presumed that such a step will be required, or prove to be desirable, for the enzyme-conjugated beads described in Example 3A, as well, and for other Enzyme-Conjugated Matrices.

EXAMPLE 2

Preparation of Purified Mixture of DNA-1 and DNA-2

A convenient volume (2 ml) of the test sample of Example 1 is prepared from pooled serum taken from inbred mice bearing myeloma MOPC-21. The dialysis step at the end of Example 1 is followed by concentration against 30% polyethylene glycol in 0.01M Tris.HCl buffer (pH 7.8). The resultant solution is further purified by chromatography on DEAE-cellulose (Whatman) using a linear KCl gradient of 0 to 1.0M in 0.01M Tris.HCl Buffer (pH 7.8). The DNA elutes at 0.45M KCL, and the eluted fractions are concentrated by dialysis against polyethylene glycol.

The resultant DNA preparation is adjusted to 0.4M in Sodium $PO_4$ buffer (pH 7.0), and heat-denatured by incubating for 16 minutes at 68° C. Distilled water is added to bring the phosphate concentration to 0.14M, and the mixture is placed on a 1 ml column of Hydroxylapatite (DNA grade, Bio-Rad Labs), which has been equilibrated in 0.01M Sodium $PO_4$ buffer (pH 7.0), boiled for 5 minutes and maintained at 68° C. After placement of the DNA mixture on the column, the column is permitted to drain by gravity, and excess fluid is discarded. Then, 6.0 ml of 0.14M Sodium $PO_4$ buffer, (pH 7.0, 68° C.) is carefully layered on the column and drained.

The double-stranded DNA of interest is then released from the column by careful application of 8.0 ml of 0.4M Sodium $PO_4$ buffer (pH 7.0). The resultant preparation of a purified mixture of double-stranded DNA is referred to as "mixed DNA-L" or "DNA-L mixture."

EXAMPLE 2A

Similar Preparation (MCDV-12)

The procedure of Example 2 is repeated with mice bearing leukemia MCDV-12.

EXAMPLE 2B

Similar Preparation (L-1211)

The procedure of Example 2 is repeated with mice bearing leukemia L-1211.

EXAMPLE 2C

Similar Preparation (Pooled MOPC 21, MCDV-12, L-1211)

The procedure of Example 2 is repeated with pooled serum taken from mice bearing myeloma MOPC-21, leukemia MCDV-12, and leukemia L-1211, respectively, so that each leukemia is represented in the DNA-L mixture.

The separation and further purification of DNA-1 and DNA-2 is achieved by fractionation of mixed DNA-L on an Enzyme-Conjugated Matrix. This is an insoluble Sepharose (Pharmacia) matrix to which R-1 DNA polymerase is covalently attached. It is prepared on the general basis, somewhat varied to meet the particular needs of this situation, of the method described in *Affinity Chromatography—Principles and Methods* (Pharmacia), which is based on the original method of Axen, Porath, and Ernback, *Chemical Coupling of Peptides and Proteins to Polysaccharides by Means of Cyanogen Halides,* Nature 214: 1302-04 (1967). Other insoluble matrices may be used instead of affinity matrices such as Sepharose, described below. For example, it is known to use glass beads, ceramics, and silica to provide a support for enzymes in enzymatic processes. The Enzyme-Conjugated Matrix must also be pretreated to bind specifically with DNA-L, as described below.

EXAMPLE 3

Preparation of Enzyme-Conjugated Matrix 1 gram of CNBr-activated Sepharose 4B (Pharmacia) is swollen in 0.001M HCl on a glass filter and washed for 15 minutes with 200 ml of 0.001M HCL. The resulting gel is washed with 0.1M $NaHCO_3$ (pH 8.3) and then with 0.1M $NaHCO_3$ (pH 8.3) containing 0.5M NaCl. The gel is then suspended in 3.5 ml of the latter buffer. Then, purified R-1 DNA polymerase (containing approximately 0.040 mg of protein in 1.0 ml of 0.28M Potassium $PO_4$ buffer (pH 6.3) with 0.001M DTT (dithiothreitol) and 20% glycerol) is added to the gel slurry, and the mixture is shaken on a wrist action shaker overnight at 4° C.

The gel is then washed twice with 0.1M $NaHCO_3$ containing 0.5M NaCl (pH 8.3), prior to blocking the remaining active groups with 1M Tris.HCl buffer (pH 8.0) for 2 hours at room temperature. Three cycles of washing the gel follow: each cycle consists of a wash with 0.1M acetate buffer containing 1M NaCl (pH 4.0) and is followed by a wash with 0.1M borate buffer containing 1M NaCl (pH 8.0).

the Sepharose gel containing the R-1 DNA polymerase, prepared in this manner, is then suspended in 5 ml of "Buffer-A" (0.054M Tris.HCl (pH 7.8), containing 0.005M 2-mercaptoethanol, 0.0001M $MnCl_2$, 0.04M KCL). A 1 ml minicolumn is then poured. The Enzyme-Conjugated Matrix is now ready for use. It may also be stored, and remains in good condition when stored at 4° C. for up to at least 3 months. This product contains approximately 10 micrograms of enzyme per ml. But results vary with each batch and an assay is required to ascertain precise enzyme content.

EXAMPLE 4

Preparation of Poly-Bead Enzyme-Conjugated Matrix

An alternative Enzyme-Conjugated Matrix has been developed by the inventor which may be simpler to use and more reliable in results than the Sepharose gel. It is based on Polybead Microparticles (Polysciences Inc., Warrington, Pa.), with carboxy groups on their surfaces. These beads are also termed "carboxylated monodisperse microspheres."

Approximately 0.1 gram of Polybead Microparticles ("beads") is thoroughly washed in Potassium $PO_4$ buffer (pH 7.2-7.6). Approximately 25 microliters of a concentrated suspension of beads is added to 75 microliters of the same Potassium $PO_4$ buffer together with 10 microliters of a 50% solution (in water) of 1-ethyl-3-3-dimethylaminopropylcarbodiimide (ECDI). The mixture is incubated at room temperature (24° C.) for 30 minutes. The beads are then washed twice with the same Potassium $PO_4$ buffer and resuspended in aliquots of 75 microliters of this buffer containing 4% glycerol. The beads are set aside and stored in this state.

Approximately 75 microliters of the foregoing stored bead product is placed in a test tube. Then, 25 microliters of purified R-1 DNA polymerase, 0.5 to 1.0 micrograms/microliter, in $PO_4$/DTT/glycerol as described in Example 3, is added until the mixture reaches 100 microliters. The mixture is then incubated for 60 minutes at 4° C.

10 microliters of 0.2M glycine (pH 7.6–8.0) or 10 microliters of a solution of bovine serum albumin (20 mg/ml) is then added slowly to the mixture and incubation is carried out for 30 minutes at room temperature (24° C.), with periodic vortexing. The beads are then washed twice with "storage buffer" (0.05M Tris pH 7.8; 0.004M Beta-mercaptoethanol; 0.04M KCl 0.2 mg/ml Bovine Serum Albumin; 0.0001M $MnCl_2$ 20% glycerol) and resuspended in 50 microliters of storage buffer. It is then set aside until used. Prior to use of the beads in the test procedure, the beads are washed in a 0.1% solution of denatured salmon sperm DNA in storage buffer, followed by a rinse in storage buffer. The product contains approximately 5.0 micrograms of enzyme per ml, but an assay is required to ascertain precise enzyme content.

EXAMPLE 5

Pretreatment of Column and Separation of DNA-1 and DNA-2

The minicolumn of Example 3 is pretreated with 5 ml of a conveniently available nonhuman, nonmurine DNA, such as alkali-denatured salmon sperm DNA (50 micrograms/ml) which is passed through the column at 4° C. The column is then washed sequentially with 10 ml of Buffer-A, 10 ml of Buffer-A plus 0.5M KCl, and 10 ml of Buffer-A again. The preparation of mixed DNA-L of Example 2 (a purified mixture of DNA-1 and DNA-2) is passed through the column and the eluate is recycled through the column over a 20-minute period.

The column is then drained and washed again with 5 ml of Buffer-A (Example 3), which is followed by elution of the DNA-L mixture with 5 ml of a linear gradient of KCl (0–1M in Buffer-A). DNA-1 elutes at 0.1M KCl; DNA-2 elutes at 0.22M KCl. Following completion of the gradient, the column is washed with 5 ml of Buffer-A containing 1M KCl. (The column can be regenerated for further use by washing with 15 ml of Buffer-A.)

Of the original input DNA, approximately 4.5% is recovered as DNA-1 and 4.6% as DNA-2.

It is possible to use a purified mixture of natural DNA-L extracted from a living source for these tests, but the inventor prefers to use a pure, cloned product. It is cheaper and more convenient, once the procedure is established. It is also believed to be scientifically more sound, since it eliminates a possible variable factor, i.e., the presence of contaminating DNAs in the DNA-L preparation, and the cloned DNA is precisely the same DNA in every test that is performed.

The inventor has therefore used a cloning procedure employing the pBR322 plasmid as cloning vector. The following example refers to DNA-1, but the procedure for cloning DNA-2 or a DNA-L mixture is substantially identical. The general approach used here is based on the method descrubed in Bahl, Marians, Wu, Stawinsky, and Narang, *A General Method For Inserting Specific DNA Sequences Into Cloning Vehicles*, Gene 1: 81–92 (1976). The method uses "linkers" sensitive to the restriction enzyme Bam I as described in Scheller, Dickerson, Boyer, Riggs, and Itakura, *Chemical Synthesis of Restriction Enzyme Recognition Sites Useful for Cloning*, Science 196: 177–80 (1977). Alternatively, the cloning method employing the single-stranded M13 phage, as described by Sanger, Coulson, Barrell, Smith and Roe, J. Molecular Biology (1980) 143: 161–178, may be employed.

EXAMPLE 6

Cloning DNA-1

Phosphorylation buffer (10X) is prepared, consisting of 0.7M Tris.HCl (pH 7.6) and 0.1M $MgCl_2$. 1 microliter of the buffer is mixed with 0.5 microliter of 0.01M ATP, 5 microliters of 0.01M DTT, 1 microliter of 4.5 mg/ml T4 Polynucleotide Kinase (New England Biolabs). Then, 500 ng of Bam linker, dissolved in 1 microliter of water, is added. Further water is added to bring volume up to 10 microliters. The mixture is incubated for 1 hour at 37° C., and is then frozen at −20° C. for storage. This mixture is referred to as "phosphorylated Bam linker" or "PBM".

A mixture is prepared containing 10 Units of T4 DNA Ligase (New England Biolabs) in 82 microliters of 0.07M Tris.HCl (pH 7.5), containing 0.007M $MgCl_2$ and 70 micro M ATP. To this is added 10 micrograms of the labeled DNA-1 of Example 6 and 1.8 micrograms of PBM in 18 microliters of water. The resulting 100 microliters of mixture is incubated at 15° C. overnight and the reaction is stopped by bringing the temperature of the mixture to 65° C. for 10 minutes. This produces a mixture containing DNA-linker molecule.

To the mixture is then added 100 Units of Bam HI in 10 microliters of water and 12 microliters of Bam 10X buffer (0.2M Tris.HCl (pH 8.0), 0.07M $MgCl_2$, 0.02M BME, 1M NaCl). the mixture is incubated at 37° C. for 3 hours, and the reaction is stopped by adding 12 microliters of 0.2M $Na_2EDTA$. This trims the PBM from the DNA-linker molecule.

The DNA-linker mixture is sequentially treated with phenol and ether to extract DNA-linker from it. The volume of the extract is reduced to 20 microliters by passing nitrogen gas over it.

The concentrated extract is passed over a 1 ml column of Sephadex G-50 (Pharmacia) equilibrated in 0.1M Tris.HCl (pH 7.8) containing 0.05M NaCl. One drop fractions are collected in microfuge tubes. The location of the DNA-linker is determined by detection of the $32_p$ label, and the volume of the solution containing DNA-linker is measured (approximately 0.1 ml). The DNA-linker is recovered by addition of 10 microliters of 3M Na Acetate and 0.2 ml of ethanol. The mixture is allowed to stand at −20° C. overnight.

The precipitated DNA-linker is then pelleted by centrifugation and dried in vacuum. The pellets are dissolved in 30 microliters of water and stored at −20° C.

1 microgram of pBR322 (BRL Labs) is treated with BAM I and bacterial alkaline phosphatase and placed in a volume of 5 microliters of water. To this is added 2 microliter of IOX Ligase buffer (20 Units T4 DNA Ligase in 2 microliters) and 1 microgram of DNA-linker pellets in 2 microliters of water. Volume is adjusted to 20 microliters by addition of water. The mixture is incubated at 15° C. overnight. As a result, the DNA-linker is now ligated into the pBR322 plasmid vector, and the mixture contains DNA-linker-pBR322 vector.

HB101 *E. coli* is then infected with the DNA-linker-pBR322 vector. Host HB101 cells are pretreated with chilled 0.1M $CaCl_2$ and are incubated at 4° C. for 15 minutes, and are recovered by centrifugation. To 0.3 ml of cell pellet are added 100 mg of the vector. The *E. coli*/vector mixture is then incubated on ice for 10 minutes and is then given a 30 second thermal shock at 37° C. The *E. coli*/vector is then incubated on ice for 90 minutes.

A "ML medium" mixture is prepared of 1% Bactopeptone, 0.5% yeast extract, and 0.5% NaCl. Then, 2 ml of ML medium is added to the *E. coli*/vector mixture, and the mixture is incubated at 37° for 60 minutes. Ampicillin is added to the mixture to bring about a concentration of 40 micrograms/ml and incubation is continued at 37° C. for 30 minutes.

0.5 ml of the mixture is plated on ML medium containing 50 micrograms/ml of Ampicillin. A separate plating is made using a 1:10 dilution of the mixture. The plates are incubated overnight at 37° C. The number of colonies is counted.

Replica plates are then made on ampicillin and tetracycline. The *E. coli* colonies of interest are those that have lost resistance to tetracycline and retained resistance to ampicillin. Approximately 5 to 10 colonies survive out of about 300 that are found on the original ampicillin-containing plates.

Each *E. coli* colony is grown separately in 10 ml ML medium for 7 hours at 37° C. Chloramphenicol is then added to reach a concentration of 100 micrograms/ml and incubation is continued at 37° C. overnight. The solutions are pooled and centrifuged to recover cell pellet. The pellet is taken up in 0.7 ml of STET buffer (0.05M Tris.HCl (pH 8.0), containing 8% sucrose, 5% Triton-X-100, 0.5M EDTA) to which 50 microliters of lysozyme (10 mg/ml) is added.

The mixture is centrifuged immediately at 12,000 g for 10 minutes at room temperature. The resulting supernatant is placed in microfuge tubes. An equal volume (approximately 0.4 ml) of isopropanol is added and the mixture is placed at −20° for 1 hour and then centrifuged.

The resulting DNA pellet is washed with ethanol, resuspended in 0.5 ml buffer (0.02M Tris.HCl (pH 8.1), containing 0.01M EDTA, 0.1M NaCl) and treated with RNAse-A (Millipore), RNAse T1 (Sigma), and Proteinase K (EM Biochemicals, Darmstadt) to respective final concentrations of 100 micrograms/ml, 25 U/ml, and 0.025 mg/ml for 5 hours at 37° C.

The mixture is then extracted with 0.5 ml of buffer saturated phenol and shaken for 5 minutes and extracted with chloroform (0.166 ml) for 5 minutes. The resultant aqueous phase is extracted with ether to remove phenol and chloroform. 0.05 ml of 3M Na Acetate is added to the aqueous phase, and then 2 volumes of cold ethanol follow. The mixture is held overnight at −20° C.

The precipitated DNA is washed with ethanol, vacuum dried, and resuspended in a suitable volume (approximately 100 ml) of 0.005M Tris.HCl (pH 7.4) containing 0.0001M EDTA.

A sample of the DNA must then be tested. Its ability to inhibit R-1 DNA polymerase confirms its identity. The DNA is tested by excising it from the pBR 322 vector. This is performed by preparing and using a "Digestion Mix." The Digestion Mix is 100 mg/ml Bovine serum albumin; 0.02M Tris.HCl (pH 7.0); 0.1M NaCl; 0.007M MgCl$_2$; and 0.002M 2-mercaptoethanol. To 0.1 ml of Digestion Mix is added 50 micrograms pBR 322 DNA with insert and 50 units of BAM HI. The mixture is incubated for one hour at 37° C.

The insert form plasmid DNA is then separated by gel electrophoresis. A 2% agarose gel is used with a buffer of 0.08M trizma base, 0.033M Na Acetate, 0.036M NaCl, and 0.004M EDTA.

An alternative cloning method may be employed. A mixture of the double-stranded DNA or "DNA-L mixture" obtained in Example 2 is rechromatographed on DEAE-cellulose (Whatman) using a linear KCl gradient of 0 to 1.0M in 0.01M Tris HCl buffer (pH 7.8). The DNA elutes at 0.44 to 0.5M and is hereafter referred to as DEAE-II DNA. The eluted fractions containing DEAE-II DNA are concentrated by dialysis against polyethylene glycol. This further purification removes degraded DNA and produces a more pure, double-stranded, heterogeneous mixture of DNAs. The mixture contains DNA-1 and DNA-2. Alternatively, DNA-1 and DNA-2 may be prepared as described in Example 5. Cloning using the bacteriophage M13 mp8 may be accomplished with any of the aforementioned DNA fractions by the following procedure:

EXAMPLE 6A

Second Cloning Procedure

DEAE II DNA is suspended in 25 microliters of a solution containing 0.067M Tris pH 8.0, 0.0067M MgCl$_2$, 0.01M 2-mercaptoethanol, and 25M dGTP, dCTP, dATP and, dTTP. Then, 0.014 unit/mg DNA of T4 DNA polymerase (Bethesda Research Laboratories, Gaithersburg, Md.) is added and incubation is carried out at 15° C. for 2 hours. This is a modification of the methods of Challberg and Englund described in Enzymology 65: 39–43 (1980). This procedure serves to create "blunt ends" on the DNA molecule.

2 micrograms of the replicative form DNA of the phage M13 mp8 (New England Nuclear, Boston, Mass.) is cleaved with SmaI restriction endonuclease (New England Biolabs, Beverly, Mass.) and precipitated with ethanol. This converts the circular replicative form to a linear DNA. The linear DNA so treated is resuspended in 25 microliters of 0.01M Tris pH 7.8, and 280 units of bacterial alkaline phosphatase (Bethesda Research Laboratories) are added. The mixture is incubated at 65° C. for one hour, after which the solution is sequentially extracted with phenol and ether.

A ligation mix is prepared containing 0.3 to 10 nanograms of blunt ended DNA, 10 nanograms of M13 phage DNA, and 80 units of T4 DNA ligase (New England Biolabs) in 0.05M Tris, pH 7.8; 0.01M MgCl$_2$; 0.02M dithiothreitol; 0.001M ATP; and 50 micrograms/ml bovine serum albumin (nuclease free, Bethesda Research Laboratories) in a 20 microliter volume. The DNA is ligated into the M13 phage by incubating this mixture overnight at 15° C., and the linear DNA is recircularized.

It is then necessary to place the recircularized DNA now containing the DNA to be cloned into a suitable host in which the DNA can replicate. This is called transfection and is carried out by a modification of the technique of Mandel and Higa (J. Molecular Biology 53: 154 (1970). *E. coli* strain JM103 is grown to log phase (A600, approximately 0.4) in 2×YT medium (16 mg/ml Bacto-Tryptone, 10 mg/ml Yeast Extract, 10 mg/ml NaCl). 25 ml of culture is placed on ice for 15 minutes, and the cells are then pelleted by centrifugation and resuspended in 10 ml of ice cold 0.01M NaCl. Following this, the cells are pelleted once again by centrifugation, resuspended in 10 ml of ice cold 0.1M CaCl$_2$, and left on ice for 20 minutes. Cells are then pelleted and resuspended in 2 ml of ice cold 0.1M CaCl$_2$ and incubated on ice for another 15 minutes. 0.3 ml of cell are then added to aliquots of the ligated DNA and placed in a 37° water bath for 30 seconds. The mix is then placed on ice for 90 minutes with occasional shaking, and the cells are then plated on medium containing isopropylthiogalactoside (IPTG) and dibromo-dichloro-indolygalactoside (xgal) by the method of Messing (Methods in Enzymology, 1983). After incubating overnight at 37° C., clear plaques are selected for further screening.

Single stranded phage DNA is then obtained using methods described by Sanger, Coulson, Barrell, Smith and Rose in J. Molecular Biology 143: 161 (1980) with some modifications. Phage plaques are recovered with a toothpick and placed into 1 ml cultures of log phase JM103 cells (A650, approximately 0.3) in 2×YT medium in 17×100 mm culture tubes. Tubes are swirled at 300 RPM for 4 to 8 hours at 37°, with caps vented to permit aeration. The contents of each tube are transferred to a 1.5 ml Eppendorf centrifuge tube and centrifuged 5 minutes in an Eppendorf centrifuge. The supernatant is poured into a second Eppendorf tube and 200 microliters of 20% polyethylene glycol 6000 in 2.5M NaCl is added. The tubes are then vortexed and incubated at room temperature for at least 15 minutes in an Eppendorf centrifuge. The supernatants are removed as thoroughly as possible, using pasteur pipets with drawn out capillary tips. The pellets are resuspended in 100 microliters of 0.01M tris. (pH 7.8) containing 0.0001M EDTA and extracted with 50 microliters of neutralized phenol. DNA is ethanol precipitated and brought to a final volume of 25 microliters. Approximately 5 micrograms of DNA is recovered by this procedure.

Five microliters of DNA solution (containing approximately 1 microgram of DNA) is combined with 1 microliter of a 15 base pair double stranded M13 primer (2.5 microgram/ml, New England Biolabs, Beverly, Mass.), 1 microliter of buffer (0.07M Tris HCl, pH 7.5; 0.07M $MgCl_2$; 0.5M NaCl) and 3 microliters $H_2O$. This mixture is drawn into a capillary tube both ends of which are flame sealed, and then placed in a tube of water (13×100 mm) at 100° C. for five minutes. The mixture is allowed to remain in the tube of water for 30 minutes while cooling to room temperature, according to the method of Anderson, Gait, Mayol, and Young described in Nucleic Acids Research 8: 1731 (1980).

The contents of each of the foregoing capillary tubes is placed in an Eppendorf tube and combined with 1 microliter of 0.1M dithiothreitol, 2 microliters of a solution 0.0022M for each of the 4 dNTP's, and 1 unit of the Klenow fragment of DNA polymerase I (New England Biolabs). The DNA containing mixtures are incubated for 20 minutes at room temperature, at which time the following were added: 0.5 microliters 1 mg/ml nuclease-free bovine serum albumin (Bethesda Research Laboratories, Gaithersburg, Md.) and 5 units each of Eco RI (Miles Laboratories, Elkhart, Ill.) and Bam HI (New England Biolabs, Beverly, Mass.). Incubation is continued for 1 hour at 37°.

Electrophoresis of the samples so obtained is performed in 2% agarose gels with a running buffer of 0.08M Tris HCl pH 7.8, 0.03M sodium acetate, 0.036M sodium chloride, 0.004M EDTA, and 0.5 micrograms/ml ethidium bromide. Gels are run submerged in a minigel apparatus. (C.B.S. Scientific, Del Mar, Cal.) at 20 m.a. constant current. The migration of the respective DNAs can be measured by observing the gels under ultraviolet light at a time when the bromophenol blue tracking dye has migrated 3 or 4 cm from the origin.

Phage from plaques found to have inserts are used to make one ml cultures as described above for screening 10 ml aliquots from 1 ml cultures frozen at −70° may be substituted for phage toothpicked directly from plaques. The phage culture is added to 200–500 ml of a log phase culture of E. coli JM 101 (A600, approximately 0.3) in 2×YT medium. This culture is shaken at 37° for 4 hours, chloramphenicol is then added to 100 micrograms/ml and incubation is continued for 2–3 more hours.

Purification of the replicative form was performed by the method of Holmes and Quiglye described in Analytical Biochemistry 114: 193 (1981). Cells are pelleted by centrifugation and washed with 0.01M Tris, 0.002M EDTA, then centrifuged and resuspended in 20–35 ml of 8% sucrose, 5% Triton×100, 0.05M EDTA, and 0.05M Tris, pH 8.0 (STET buffer), 20–50 microliters of a 50 mg/ml stock solution of lysozyme (Worthington Biochemicals, Freehold, N.J.) is added. The cell suspension is brought to a boil over a flame, placed in a boiling water bath for 40 seconds and immediately spun at 12,000×G for 10 min. The supernatant containing the replicative form DNA is decanted and the DNA precipitated with isopropanol. The replicative form is further purified by CsCl density gradient centrifugation using ethidium bromide. Ethidium bromide is removed from the DNA solution by two extractions with CsCl saturated isopropanol. The samples are then dialyzed against 0.01M Tris, pH 7.8; 0.0001M EDTA and concentrated against 30% polyethylene glycol in the same buffer.

The restriction enzymes, Bam HI and Eco RI are used to excise inserts, which are separated from vector DNA on 2% agarose gels run as described for the screening procedure above. Insert bands are electroeluted into troughs cut in the agarose, using the method of Yang, Lis and Wu, Methods in Enzymology 68: 176 (1979), ethanol precipitated, and reconstituted with an appropriate buffer.

Analytic tests have been performed on cloned DNA-L in order to ascertain the identity of the DNA with greater specificity. Partial sequences of three DEAE-II DNAs, cloned from MOPC-21 tumor tissue, are listed below:

|   | Clone "A" Sequence (210 bp long) | | |
| --- | --- | --- | --- |
| 1<br>AACCACGCTT | 11<br>TTGCCAACCG | 21<br>AACACCATTG | 31<br>GGTGATGCCA |
| 41<br>TCGATTCAAC | 51<br>ATATTTGCTG | 61<br>TCGGTGCAGA | 71<br>GCCGCATCTG |
| 81<br>ACACGGTTGG | 91<br>TTCAACGCGC | 101<br>AGATCACGGC | 111<br>GGTCATTTCC |

-continued

| 121 | 131 | 141 | 151 |
|---|---|---|---|
| ATGCGGTTGT | TGGTGGTCTG | CGGCTCGGAG | CCGACCAGTT |

161
CCTTCTCCT...

Clone "B" Sequence

| 1 | 11 | 21 | 31 |
|---|---|---|---|
| TTATCAGTGA | TTACATATCA | TTTGAGTTCT | TTTGTGATTG |
| 41 | 51 | 61 | |
| TGTTACTCAC | TCAGGCTCAT | TGTGTGA... | |

Clone "C" Sequence

| 1 | 11 | 21 | 31 |
|---|---|---|---|
| TGATTTTCAG | ATTTCTTGCC | ATATTCCACG | TCCTACAGTG |
| 41 | | | |
| GCATTTCTA... | | | |

III. Labeling of DNA

After cloning the DNA-1, it may be desirable to "label" it to facilitate verification of parts of the cloning procedure. Moreover, the malignancy test procedures described below require use of "labeled" DNA, that is, DNA that is physically or chemically treated, so that it can be followed and measured through subsequent procedures. Typically, radioactive material is used to label molecules for such purposes. The inventor has found that phosphorous 32 ($^{32}P$) and tritium ($^3H$) are particularly useful and effective isotopes for labeling DNA-L. It also is known in the art to use optically active labels such as dyes or fluorescent complexes and to use radioopaque agents, to assist in visualizing the thus-labeled substance. It is therefore intended to include within the concept of labeling (as subsequently claimed) all such equivalent means.

Further, the labeled DNA used for competitive binding may be a modified cancer DNA selected for its affinity with the enzyme to which the natural cancer DNA of the test binds; in such event, the modified DNA can be used in lieu of naturally-derived DNA for the DNA probe of the test.

A radioactive label is inserted into the DNA molecule by an enzymatic process, as described below. The following example refers to DNA-1 but the procedure for DNA-2 or cloned DNA from DNA-1, DNA-2, or DNA-L is substantially identical. The term "DNAse I" used below refers to a bacterial enzyme capable of introducing single strand breaks or gaps in double-stranded DNA molecules. The DNAse I enzyme used here is that obtained from Millipore Corp., but there are other suppliers.

EXAMPLE 7

Labeling DNA-1 With $^{32}P$

A mixture containing 5000 microCuries of a carrier-free radio-labeled ($^{32}P$) deoxynucleoside triphosphate (dCTP) labeled in the alpha position is prepared in 1.0 ml of 0.01M Tris.HCl buffer (pH 7.4). Separate solutions of each of four unlabeled deoxynucleoside triphosphates (known in the art as dCTP, dATP, dGTP and TTP) are prepared, containing 0.2 nanomoles/microliter and using the same buffer. A mixture is then prepared containing 20 microliters of the radio-labeled $^{32}P$ deoxynucleoside triphosphate, 10 microliters of each of the unlabeled deoxynucleoside triphosphates dGTP, dATP, and TTP, and 2 microliters of unlabeled dCTP. This is followed by 10 microliters of 10× reaction buffer and 2 micrograms of the DNA of Example 6 in 2 microliters. After mixing, distilled water is added to bring the total volume to 97 microliters. This is referred to as "Labeling Mixture."

"Activation buffer" is prepared by mixing 10 ml Tris.HCl (pH 7.6); 0.005M $MgCl_2$; and 1 mg/ml nuclease-free BSA. 9 microliters of Activation Buffer is mixed with 1 microliter of a solution containing 100 micrograms/ml of DNAse I (equivalent to 0.1 microgram DNAse I), and the mixture is left at 4° C. for 2 hours. This mixture is referred to as "Activated DNAse I."

One microliter of Activated DNAse I is added to 97 microliters of Labeling Mixture, and the resulting mixture is incubated for 10 minutes at 15° C. To that mixture is then added two units of *E. coli* DNA polymerase I (1 Unit/microliter) in 2 microliters of Potassium $PO_4$ (pH 7.0) buffer. The buffer is 0.001M in 2-mercaptoethanol and contains 50 percent glycerol. The reaction is continued for one hour, and is stopped by addition of 0.2 ml of 0.3M $Na_2EDTA$ (pH 8.0). The DNA is then separated from residual nucleotides by chromatography on a column of Sephadex G-50 (fine grade) (Pharmacia) previously equilibrated in a suitable volume of 0.01M Tris.HCl containing 0.0001M $Na_2EDTA$ (pH 8.0).

EXAMPLE 7A

Labeling DNA With Fluorescent Dye (Ethidium Bromide)

To 1.0 ml of 0.1% solution of Ethidium Bromide is added 1.0 ml of solution containing 10 micrograms DNA-L/ml. The mixture is subjected to gel filtration on a column of Sephadex G-10 to remove unreacted Ethidium Bromide. The labeled DNA-L is recovered in 0.01M Tris.HCl containing 0.0001M $Na_2EDTA$ (pH 8.0), as at the end of Example 6.

The Ethidium Bromide intercalates between the strands of the DNA double helix. It is excitable at 518 nm and emits at 610 nm.

EXAMPLE 7B

Labeling DNA By Fluorescent Antibody Technique

A "nick translation" technique similar to that of Example 7 may be used with biotinylated deoxyuridine triphosphate (dUTP). A procedure is described in Gardner, *Non-radioactive DNA Labeling: Detection of*

*Specific DNA and RNA Sequences on Nitrocellulose and in situ Hybridizations,* Biotechniques 1: 38–41 (1983).

The biotinylated dUTP is substituted for the $^{32}P$ labeled deoxynucleoside triphosphate of Example 7, paragraph 1. Thus, 100 n moles of biotinylated deoxynucleoside triphosphate (dUTP) is made up in 2 microliters of 0.01M Tris (pH 7.4). Separate solutions of non-biotinylated deoxynucleoside triphosphates (dATP, dCTP, dAMP, TTP) are made up in the same buffer concentrations such that 2 microliters will contain 50 n moles of each of the non-biotinylated deoxynucleoside triphosphates. A mixture is then prepared containing 2 microliters of the biotinylated dUTP and 2 microliters of each of the non-biotinylated deoxynucleoside triphosphates. This is followed by 10 microliters of $10\times$ reaction buffer and 2 micrograms of the DNA of Example 6 in 2 microliters. After mixing, distilled water is added to bring the total volume to 97 microliters. This is referred to as "Labeling Mixture."

The procedure described in paragraphs 2 and 3 of Example 7 is then followed.

The biotin is then detected on the biotinylated DNA with an antibody, specifically an IgG fraction of goat anti-biotin and a fluorescein isothiocyanate (FITC)-conjugated rabbit anti-goat antibody (Enzo Biochem Inc.). The goat anti-biotin binds to the biotin in the DNA, which is then followed by binding of the FITC rabbit anti-goat antibody to the goat-anti-biotin. The DNA is approximately equal in molecular weight to that of immunoglobuline. Therefore, 1 microgram of biotinylated DNA is reacted with 1 microgram of the IgG fraction of goat anti-biotin, followed by reaction with 1 microgram of FITC conjugated rabbit anti-goat antibody. The entire complex of DNA and antibodies is used in the test in the same manner as radio-labeled DNA.

IV. Preparation of Enzyme-Conjugated Matrix and Purification Matrix for Tests There may be a number of enzymes in other tissues from other species capable of being selectively inhibited by DNA-L. Although the inventor has thus far found only one that is effective in these tests, it is believed that trial and error procedures would develop others useful in these tests on the basis of the techniques described herein, and they are considered within the scope of this invention. The enzyme used here is R-1 DNA polymerase, extracted from murine myeloma tumor by the procedure described in Analytic Biochemistry 87: 411 (1978), supra. The inventor has tested R-1 DNA Polymerase with samples of other DNAs that may be present in blood and other body fluids, and found that none of those DNAs appeared to specifically inhibit (selectively bind with) the R-1 DNA polymerase.

EXAMPLE 8

Preparation of Enzyme-Conjugated Matrix for Tests

The procedure of Example 3 or 4 is carried out, using the same CNBr-activated-Sepharose or Poly-Beads. The pretreatment procedure of Example 5 is carried out. The enzyme content is assayed by the procedure described in Gottlieb et al., Cancer Research 40: 758–770 (1980), supra, and recorded.

The resulting product is an R-1 DNA polymerase Enzyme-Conjugated Matrix suitable for use in the tests described herein. It remains stable at 4° C. for at least 3 months. It may be regenerated for repeated use by washing with 1M KCl followed by assay buffer.

Serum samples can contain small amounts of "extraneous DNAs," i.e., DNAs that are unrelated to DNA-L. Such extraneous DNAs could interfere with the accuracy of the test by binding to some of the R-1 DNA polymerase on the Enzyme-Conjugated Matrix. However, such extraneous DNAs will not be specific to R-1 DNA polymerase. Therefore, they can be "cleaned up" by use of an extraneous enzyme on an appropriate matrix. The enzyme Reverse Transcriptase, which is derived from Rauscher Leukemia Virus, is not inhibited by DNA-1, DNA-2, or DNA-L, but it *is* inhibited by a wide variety of the other, extraneous DNAs. A method of preparing the enzyme is described in Ross, Scolnik, Todaro, and Aaronson, Nature New Biology 23i: 163–70 (1971). This enzyme can be used to prepare a Purification Matrix for the test sample, as described below.

EXAMPLE 8A

Preparation of Purification Matrix for Tests

Approximately 0.1 gram of Polybead Microspheres is washed in Potassium $PO_4$ buffer (pH 7.2–7.6). Approximately 25 microliters of a concentrated suspension of beads is added to 75 microliters of the same Potassium $PO_4$ buffer together with 10 microliters of a 1 gram/ml solution of 1-ethyl-3-3-dimethylaminopropylcarbodiimide in $H_2O$ (ECDI). The mixture is incubated at room temperature (24° C.) for 30 minutes. The beads are then washed with the same Potassium $PO_4$ buffer and resuspended in aliquots of 75 microliters of this buffer containing 4% glycerol. The beads are set aside and stored in this state.

Approximately 75 microliters of the foregoing stored bead product is placed in a test tube. Purified Reverse Transcriptase (0.5 to 1.0 microgram/microliter) is added until the mixture reaches 100 microliters. The mixture is then incubated for 30 minutes at room temperature (24° C.).

10 microliters of 0.2M glycine (pH 7.6–8.0) *or* 10 microliters of a solution of bovine serum albumin (20 mg/ml) is then added slowly to the mixture and incubation is carried out 30 minutes at room temperature (24° C.), with periodic vortexing. The beads are then washed twice with "storage buffer" (0.05M Tris pH 7.8; 0.004M Beta-mercaptoethanol; 0.04M KCl 0.2 mg/ml Bovine Serum Albumin; 0.0001M $MnCl_2$ 20% glycerol) and resuspended in 50 microliters of storage buffer. It is then set aside until used. Prior to use, the beads are worked washed in a 0.1% solution of denatured salmon sperm DNA in storage buffer, followed by a rinse in storage buffer. This product is "Purification Matrix."

EXAMPLE 8B

Use of Purification Matrix to Purify Test Sample

Approximately 1 cc of test sample of Example 1 is mixed with 10 microliters of Purification Matrix of Example 8A. The mixture is thoroughly shaken and set aside for 30 minutes at room temperature (24° C.). It is then centrifuged for 10 minutes at 1000 g.

The supernatant is "purified test sample." The beads may be recovered and recycled.

V. Test Procedure

As already indicated, the invention detects presence of cancer DNA (DNA whose production in appreciable quantity is associated with malignancies) by means of "competitive binding." Labeled cancer DNA "competes" with (i.e., acts as a DNA probe for) any cancer DNA occurring in the test subject's blood (or other body fluid) for binding sites on the enzyme in the Enzyme-Conjugated Matrix. Since the Enzyme-Conjugated Matrix has been pretreated with other DNA (such as salmon sperm DNA), those binding sites on the Enzyme-Conjugated Matrix that have a general affinity for DNA (rather than a selective affinity for the cancer DNA of interest, such as DNA-L) are already tied up and thus do not interfere with the test procedure. Also, the possibility of extraneous DNAs being present, that could interfere with the test because they will bind with any of a number of enzyme sites, possibly including R-1 DNA polymerase, is obviated by pretreating the test sample with a Purification Matrix. The proportion of labeled cancer DNA taken up and bound to the Enzyme-Conjugated Matrix is related to the presence or absence of competing cancer DNA in the test subject's blood (or fluid). If no competitive cancer DNA is present, a maximum amount of labeled cancer DNA is bound to the Enzyme-Conjugated Matrix. But if competitive DNA is present, a lesser amount of labeled DNA is bound to the Enzyme-Conjugated Matrix. The proportion of labeled DNA (DNA probe) bound to the Enzyme-Conjugated Matrix under these conditions is thus an indicator of the presence of cancer DNA in the test subject's blood or fluid.

The test procedure involves the steps of preparing a test sample from the test subject's blood or fluid (Example 1); purifying it with Purification Matrix (Examples 8A and 8B); mixing labeled DNA (Example 7), preferably cloned (Example 6) rather than natural, with the purified test sample; "introducing" the test sample containing labeled DNA ("DNA/sample mixture") to an Enzyme-Conjugated Matrix (Example 8); and, finally, determining how much labeled DNA has become bound to the Enzyme-Conjugated Matrix.

To "introduce" the DNA/sample mixture to the Enzyme-Conjugated Matrix, a known quantity of the DNA/sample mixture is mixed with buffer and a known quantity of pretreated Enzyme-Conjugated Matrix of Example 8. The latter contains a known quantity of enzyme. The resulting mixture is then incubated for 15 minutes at 25° C. The matrix is then separated from the fluid residue of the DNA/sample mixture and buffer, by centrifugation. To obtain best results, the relative concentrations of labeled DNA and Enzyme-Conjugated Matrix should have a relationship such that, at anticipated concentrations of the cancer DNAs of interest (which, in the case of leukemia, is DNA-L) in the test sample, there is a considerable difference (e.g. 10% versus 90%) between the results of a test on a normal blood sample and one on a "malignant" blood sample. This result may be advantageously accomplished when: (1) the amount of DNA-L added to the test sample slightly exceeds the amount of enzyme in the Enzyme-Conjugated Matrix (in terms of molecules), so that the added DNA-L can bind with all of the sites on the enzyme and still leave a slight excess of DNA-L; and (2) the amount of natural DNA-L present in the test sample, if the patient has a malignancy, is at least several times the amount of enzyme (in terms of molecules).

The inventor believes that 1 molecule of DNA binds to 1 molecule of enzyme; that the molecular weight of the DNA-L is approximately equal to 0.65 of the molecular weight of the R-1 DNA polymerase enzyme, so that 0.65 nanogram of pure DNA-L and 1.0 nanogram of pure enzyme each represent the same number of molecules (i.e., of DNA-L or enzyme, respectively); and that 0.65 nanogram of DNA-L binds with 1.0 nanogram of R-1 DNA polymerase, and so on. Further, it is believed that the M.W. of the enzyme is approximately 200,000, and that the M.W. of the DNA-L is approximately 130,000. The examples that follow are described in terms of purified DNA-L and preparations of R-1 DNA polymerase enzyme purified substantially to homogeneity.

There are at least two ways to test for take-up of labeled DNA. One is to test the residual fluid that remains after the removal of the Enzyme-Conjugated Matrix. If x percent of labeled DNA (DNA probe) remains in the residual fluid, 100−x percent was bound to the Enzyme-Conjugated Matrix. The other way is to test the Enzyme-Conjugated Matrix, by extracting from it substantially all of the bound, labeled DNA and measuring the latter. Ideally, the two methods are complementary, and the sum of the two amounts of labeled DNA (in the residual fluid and in the Enzyme-Conjugated Matrix) should be equal to the amount of labeled DNA added to the test serum.

Unfortunately, this does not occur, due to experimental errors. The first method, the residual fluid assay method, is believed to be the most accurate. The second method, the matrix assay method, involves losses in washing, inadequate extraction, etc., that are believed to amount to about 25%. This estimate is based on the inventor's tests using a test serum with 100% labeled DNA-L, the DNA-L being present in excess of the available sites, so that about 50% would be in each moiety; performing both assay methods; and attributing all loss to the matrix assay method.

The preferred embodiment, at least for DNA-L and the leukemia test, is therefore the residual fluid assay method, rather than the matrix assay method, although the latter is a check on the former. It may also be noted that the procedures of the matrix assay method are more laborious and time-consuming than those of the residual fluid assay method.

The following examples all refer to DNA-1. In all respects known to the inventor, DNA-2 produces identical results to DNA-1, and it makes no difference known to the inventor which one is used, or whether a mixture is used that contains DNA-1 and DNA-2. Also, no difference is found between the results of tests using cloned DNA-L originally obtained, respectively, from humans or mice, although human and mouse DNA-L are believed not to be identical. However, there may be differences in result that arise from the use of various cloned DNAs and sera from various patents with different lymphoid cancers.

EXAMPLE 9

Test of Normal Mouse (Residual Fluid Assay Method)

1.0 cc of serum is obtained from a laboratory mouse believed to be normal. Test sample is prepared in accordance with Example 1, and purified in accordance with Examples 8A–8B.

To 0.5 cc of the purified test sample, 0.5 cc is added of an aqueous buffered mixture containing the labeled DNA-1 solution of Example 7. The DNA solution contains 1.0 micrograms/cc of the pure, labeled, cloned DNA-1 of Example 6, or a total of 500 nanograms. The solutions are thoroughly mixed, and the resulting DNA/sample mixture is then ready for "introduction" to the Enzyme-Conjugated Matrix.

0.5 ml of a suspension of assayed and pretreated Enzyme-Conjugated Matrix containing 650 nanograms of R-1 DNA polymerase enzyme is added to the DNA/-sample mixture. After incubation at 25° C. for 15 minutes, the matrix is recovered by centrifugation, and put aside.

The residual fluid is collected. It is tested for labeled DNA-1 by liquid scintillation spectrometry. It is found the residual fluid contains 78 nanograms of labeled DNA-1. This is 16% of the amount originally in the DNA/sample mixture.

The mouse is kept alive for 30 days and is then sacrificed, at which time it shows no signs of malignancy.

EXAMPLE 10

Test of Normal Mouse (Matrix Assay Method)

The test of Example 9 is repeated, but the assay is performed on the matrix by liquid scintillation spectrometry.

It is found that the matrix has bound to it 28 nanograms of labeled DNA-1. This is 56% of the amount originally in the DNA/serum mixture.

EXAMPLE 11

Test of Mouse With Known Leukemia

The procedure of paragraphs 1 through 3 of Example 9 are repeated with a laboratory mouse known to have multiple myeloma. The residual fluid assay method is used.

It is found that the residual fluid contains 410 nanograms of labeled DNA-1. This is 82% of the amount originally in the DNA/sample mixture. The ratio of this percentage to that of Example 9 (normal mouse) is approximately 5.1 to 1.

The mouse is sacrificed. Examination at autopsy reveals typical signs of myeloma.

To demonstrate the sensitivity of the test method, for use in early detection of small colonies of leukemia cells, a diluted leukemia sample may be prepared. A purified test sample from the mouse of Example 11 is therefore diluted with a purified test sample from the normal mouse of Example 9, in the ratio 1:1000. The prior test procedure is varied to account for the lesser amount of DNA-L anticipated to be present.

EXAMPLE 12

Dilution Test of Mouse With Known Leukemia

The test procedures of Example 9 are followed on the diluted purified test sample. To 0.5 cc of the diluted purified test sample is added 0.5 cc of an aqueous buffered mixture containing 1.0 nanograms/cc of the pure, labaled, cloned DNA-1 of example 7, i.e., a total of 0.5 nanogram. Similarly, 0.65 nanogram of enzyme is used. The use of the residual fluid assay method indicates that the residual fluid contains 0.4 nanograms of labeled DNA, which is 80% of the original amount.

The same test is repeated with the unmixed "normal" test serum of Example 9. The use of the residual fluid assay method indicates that the residual fluid contains 0.08 nanogram of labeled DNA-1, which is 16% of the original amount. The ratio of the two percentages is 5 to 1.

EXAMPLE 13

Test of Normal Human Subject 1.0 cc of serum is obtained from a human subject believed to be normal. Test sample is prepared in accordance with Example 1 and purified in accordance with Examples 8A–8B.

To 0.5 cc of the purified test sample, 0.5 cc is added of an aqueous buffered mixture containing cloned DEAE-II solution, labelled in accordance with Example 7. The DNA solution contains 1.0 micrograms/cc of the pure, labeled, cloned murine DNA-L of example 6A, or a total of 500 nanograms. The solutions are thoroughly mixed, and the resulting DNA/sample mixture is then ready for "introduction" to the Enzyme-Conjugated Matrix.

0.5 ml of a suspension of pretreated and assayed Enzyme-Conjugated Matrix containing approximately 650 nanograms of pure R-1 DNA polymerase enzyme is added to the DNA/sample mixture. After incubation at 25° C. for 15 minutes, the matrix is recovered by centrifugation, and put aside for recycling.

The residual fluid is collected. It is tested for labeled DNA-1 by liquid scintillation spectrometry. It is found that the residual fluid contains 70 nanograms of labeled DNA. This is 14% of the amount originally in the DNA/sample mixture.

The subject is examined after six months and appears to show no sign of leukemia.

EXAMPLE 14

Test of Human With Known Leukemia

The procedures of paragraphs 1 through 3 of Example 13 are repeated with a human patient known to have leukemia. The residual fluid assay method is used.

It is found that the residual fluid contains 430 nanograms of labeled DNA. This is 86% of the amount originally in the DNA/sample mixture. The ratio of this percentage to that of Example 13 (normal human subject) is approximately 6.1 to 1.

Examination at an autopsy of the patient reveals typical signs of leukemia.

To demonstrate the sensitivity of the test method, for use in early detection of small colonies of leukemia cells, a diluted leukemia sample may be prepared. A sample of purified test serum from the human test subject of Example 14 is therefore diluted with a purified test sample from the normal human subject of Example 13, in the ratio 1:1000. The prior test procedure is varied to account for the lesser amount of DNA-L anticipated to be present.

EXAMPLE 15

Dilution Test of Human Test Subject With Known Leukemia

The test procedures of Example 13 are followed on the purified diluted test sample. To 0.5 cc of the purified diluted test sample is added 0.5 cc of an aqueous buffered mixture containing 1.0 nanogram/cc of the pure, labeled, cloned DEAE-II DNA of Example 6A, i.e., a total of 0.5 nanogram. Similarly, 0.65 nanogram of enzyme is used. The use of the residual fluid assay method indicates that the residual fluid contains 0.42 nanograms of labeled DNA, which is 84% of the original amount.

The same test is repeated with the unmixed "normal" test serum of Example 13. The use of the residual fluid assay method indicates that the residual fluid contains 0.09 nanogram of labeled DNA, which is 18% of the original amount. The ratio of the two percentages is 4.7 to 1.

VI. Kits

To facilitate large scale screening and testing believed necessary to satisfy FDA requirements (i.e., demonstration of absence of false positives and negatives under "double blind" conditions), and to permit performance of the test by relatively unskilled laboratory personnel, a modified procedure has been developed using test kits and a dedicated test apparatus.

First, a standardized test procedure involving premixed reagents is used, so that the test may readily be performed. The kit consists of previously prepared labelled DNA material, where the label is a fluorescent dye (including fluorescent complexing agents); previously prepared Enzyme-Conjugated Matrix, and previously prepared "purification matrix." Second a dedicated fluorescence measurement device is used, which is specially adapted and calibrated for the leukemia test procedure. This procedure may not be as accurate as the radio-assay procedure described above, but it is much easier and much cheaper. (Radioactive labeling may be used instead, but the radio assay apparatus is much more expensive than the fluorescence assay apparatus described below.)

EXAMPLE 16

DNA for Kit

Pure, cloned DEAE-II DNA is prepared from DNA-L obtained from the serum of a patient known to have died from leukemia. The method of Example 6A is used.

The following are mixed in 1.0 cc of a 0.005M Tris.HCl buffer (pH 7.4): 0.5 mg of the DNA of the preceding paragraph; labeled with a fluorescent label in accordance with Example 7A. (Radioactive labeling, e.g., with $^{32}P$ or $^3H$ is an alternative expedient, as indicated above. The procedure of Example 7B may also be used.) After mixing, saline solution, U.S.P. (such as Baxter Laboratories), is added to bring total volume to 500 cc.

Into each of approximately 1000 1.0 cc vials is pipetted 0.5 cc (500 nanograms of labeled DNA) of the mixture of the preceding paragraph. The vials ("DNA vials") are sealed and placed in a refrigerator for storage at approximately 5° C.

The contents of a DNA vial are poured into a 100 ml graduate. Saline solution is added to bring volume to 50 ml. Into each of approximately 100 1 cc vials is pipetted 0.5 ml (5 nanograms of DNA) of the diluted DNA solution. The vials ("1:100 DNA vials") are sealed and placed in a refrigerator for storage at approximately 5° C.

EXAMPLE 17A

Enzyme-Conjugated Matrix for Kits

Approximately 10 grams of the Polybead Microparticles ("beads") of Example 4 is washed in Potassium $PO_4$ buffer (pH 7.4). Approximately 250 ml of a concentrated suspension of beads is added to 750 ml of the same $PO_4$ buffer together with 100 ml of ECDI (1 gram/ml water). The mixture is incubated at room temperature for 1 hour. The beads are then washed with the same buffer and resuspended in buffer containing 4% glycerol.

Approximately 750 ml of the bead product is placed in a beaker. Purified R-1 DNA polymerase, as described in Example 3, known by assay to contain approximately 8 micrograms/ml of enzyme, is added until the mixture reaches approximately 1.0 l. The mixture is incubated for approximately 1 hour at 4° C. The beads now contain a total of approximately 2 mg of R-1 DNA polymerase enzyme.

100 ml of 0.2M glycine (pH 7.6–8.0) *or* 100 ml of a solution of bovine serum albumin (20 mg/ml) is then added slowly to the mixture and incubation is carried out for 30 minutes at room temperature (24° C.), with periodic vortexing. The beads are then washed twice with "storage buffer" (0.05M Tris pH 7.8; 0.004M Beta-mercaptoethanol; 0.04M KCl 0.2 mg/ml Bovine Serum Albumin; 0.0001M $MnCl_2$ 20% glycerol); and are resuspended in 50 ml of storage buffer. The mixture is assayed for enzyme content in accordance with the method described in Cancer Research 40: 758–70, supra. The enzyme content of 0.5 ml of the mixture slightly exceeds 650 nanograms. Enough of the bead product resulting from paragraph 1 of this Example is added to the assayed mixture to reduce the enzyme content of 0.5 ml of the mixture to 650 nanograms.

To the foregoing mixture, 5 cc of 1 mg/ml alkali-denatured salmon sperm DNA (Millipore Corp.) is added, with stirring at 4° C. The mixture is stirred slowly at 4° C. for 30 minutes. The material is then washed in storage buffer, and stored in a suitable volume of storage buffer, to bring volume to 1.5 l.

In each of approximately 3000 1.0 cc vials, is placed 0.5 cc of the foregoing (650 ng of enzyme). The vials ("matrix vials") are sealed and placed in a refrigerator for storage at approximately 5° C.

The contents of a matrix vial are poured into a 100 ml graduate. Saline solution is added to bring volume to 50 ml. Into each of approximately 100 1 cc vials is pipetted 0.5 ml of the diluted solution. The vials ("1:100 matrix vials") are sealed and placed in a refrigerator for storage at approximately 5° C.

EXAMPLE 17B

Purification Matrix for Kits

Approximately 10 grams of the Polybead Microparticles ("beads") of Example 3A is washed in Potassium $PO_4$ buffer (pH 7.4). Approximately 250 ml of a concentrated suspension of beads is added to 750 ml of the same $PO_4$ buffer together with 100 ml of ECDI (1 gram/ml water). The mixture is incubated at room temperature for 1 hour. The beads are then washed with the same buffer and resuspended in buffer containing 4% glycerol.

Approximately 750 ml of the bead product is placed in a beaker. Approximately 25 mg of purified Reverse Transcriptase in 250 ml water, as described in Example 8A, is added until the mixture reaches approximately 1.0 . The mixture is incubuated for approximately 1 hour at 4° C.

100 ml of 0.2M glycine (pH 7.6–8.0) *or* 100 ml of a solution of bovine serum albumin (20 mg/ml) is then added slowly to the mixture and incubation is carried out for 30 minutes at room temperature (24° C.), with periodic vortexing. The beads are then washed twice with "storage buffer" (0.05M Tris pH 7.8; 0.004M Beta-mercaptoethanol; 0.04M KCl 0.2 mg/ml Bovine Serum Albumin; 0.0001M $MnCl_2$ 20% glycerol); and are resuspended in 50 ml of storage buffer.

To the foregoing mixture, 5 cc of 1 mg/ml alkali-denatured salmon sperm DNA (Millipore Corp.) is added, with stirring at 4° C. The mixture is stirred slowly at 4° C. for 30 minutes. The material is then washed in storage buffer, and stored in a suitable volume of storage buffer, to bring volume to approximately 1.5 l.

In each of approximately 3000 1.0 cc vials, is placed 0.5 cc of the foregoing. The vials ("matrix vials") are sealed and placed in a refrigerator for storage at approximately 5° C.

EXAMPLE 18

Use of Kit

A test sample is prepared in accordance with Example 1. Into a 2 cc vial ("test vial") is placed 0.5 cc of the test sample. Then, a purification matrix vial of Example 17B is opened and poured into the same 2 cc test vial. The mixture is thoroughly shaken for 15 minutes at 25° C. (room temperature). The test vial is centrifuged (1000 g) to separate the beads and a supernatant fluid. (The beads are recovered and recycled.) The supernatant is recovered and placed into the same or another 2 cc test vial. A DNA vial of Example 16 is opened and added to the supernatant in the 2 cc test vial. The two solutions are thoroughly mixed by vigorous shaking.

A matrix vial of Example 17A is opened and poured into the 2 cc test vial. The solutions are thoroughly mixed by vigorous shaking. The test vial is set aside for 15 minutes at room temperature (25° C.).

The test vial is subjected to centrifugation (1000 g) to separate the beads and a supernatant fluid. (The beads are recovered and set aside for recycling.)

GENERAL CONCLUSORY REMARKS

The foregoing procedures provide an entirely new diagnostic method, hitherto unknown to medical science. It is believed significant that these procedures use pure, laboratory-produced reactants (such as cloned DNA) rather than (except for the enzyme) substances that must be obtained from donors and then be purified. The procedures described above utilize DNA-L (the DNAs referred to as DNA-1 and DNA-2), but the inventor believes that other DNAs associated with other malignancies (i.e., other than that of the lymphoid system) will be isolated and be found useful in tests that are slight variations of the tests described above, and accomplish the same type of result in the same way.

Moreover, other matrices may be utilized to prepare a suitable Enzyme-Conjugated Matrix. Other resins may be used and so too many polystyrene and latex beads, to which the enzyme may be chemically bonded. Examples of the latter are hydrophilic latex spheres ("Covaspheres MX" or "FX," Covalent Technology Corp., Ann Arbor, Mich.). The invention may be practiced with any substantially insoluble material to which the enzyme can be bound, since any such material can be utilized to prepare an Enzyme-Conjugated Matrix. other enzymes having a selective affinity with (i.e., capable of selectively binding with) the pertinent DNA may be utilized. Hence, the term "Enzyme-Conjugated Matrix" used herein is intended to include any such matrix substance to which any enzyme can be attached that will selectively bind with (or be selectively inhibited by or "have a selective affinity for") the DNAs described herein.

While the invention has been described primarily in connection with a specific and preferred embodiment thereof, it will be understood that it is capable of further modifications without departing from the spirit and scope thereof. Some such modifications are described above. This application is intended to cover all variations, uses, or adaptations of the invention, following, in general, the principles of the invention and including such departures from the present disclosure as come within known or customary practice within the art to which the invention pertains, or as are obvious to persons skilled in the art.

What is claimed and desired to be secured by United States Letters Patent is:

1. A test procedure for determining the presence of a malignancy in human or animal test subjects, comprising the following steps:
   (1) preparing a test sample from a body fluid sample collected from the test subject;
   (2) mixing said test sample with a preparation containing labelled DNA-L;
   (3) introducing said mixture to an Enzyme-Conjugated Matrix, said matrix having R-1 DNA polymerase bound thereto as the conjugated enzyme; and
   (4) performing an assay to determine the proportion of said labelled DNA-L bound to said Enzyme-Conjugated Matrix or not bound thereto, as a measure of the presence of a malignancy.

2. The method of claim 1 wherein the malignancy is a leukemia.

3. The method of claim 1 wherein there is an additional step, between the first and second steps, said additional step being one in which the test sample is purified of extraneous DNA by use of a purification matrix.

4. The method of claim 1 wherein the Enzyme-Conjugated Matrix is pretreated, before step (3), with at least one DNA other than DNA-L.

5. The method of claim 1 wherein said DNA is labeled with a fluorescent dye.

6. The method of claim 1 wherein said DNA is labelled with a member of the group consisting of phosphorous 32 and tritium.

7. An article comprising:
   a support means;
   bound directly to said support means, R-1 DNA polymerase enzyme; and
   bound directly to said enzyme and bound indirectly to said support means, a quantity of labelled DNA-L.

8. A test procedure for determining the presence of leukemia in human patients, comprising the following steps:
   (1) preparing a test sample from blood collected from the patient;
   (2) mixing said test sample with a preparation containing labeled DNA-L;
   (3) introducing said mixture to an Enzyme-Conjugated Matrix to which R-1 DNA polymerase is bound as the conjugated enzyme;
   (4) performing an assay to determine the proportion of labelled DNA-L bound to the Enzyme-Conjugated Matrix or not bound thereto, as a measure of the presence of leukemia.

9. The method of claim 8 wherein, before step (3), the Enzyme-Conjugated Matrix is pretreated with a DNA other than DNA-L.

10. An article of manufacture comprising:
a first container containing a premeasured quantity of labeled DNA-L, said DNA-L being substantially pure and substantially free of other DNAs; and
a second container containing Enzyme-Conjugated Matrix, said Enzyme-Conjugated Matrix having bound thereto a premeasured quantity of R-1 DNA polymerase.

11. The article of claim 10 wherein the DNA-L is labeled with a fluorescent dye.

12. The article of claim 10 wherein the number of molecules of DNA-L in the first container is slightly greater than the number of active enzyme sites on the enzyme in the second container.

13. The article of claim 10 wherein there is a third container containing purification matrix.

* * * * *